US007018351B1

(12) United States Patent
Iglesias et al.

(10) Patent No.: US 7,018,351 B1
(45) Date of Patent: Mar. 28, 2006

(54) COMFORTABLE ORTHOPAEDIC SUPPORT AND THE METHOD OF MAKING THE SAME

(75) Inventors: Joseph M. Iglesias, Newbury Park, CA (US); Eric E. Johnson, Carlsbad, CA (US); Tracy E. Grim, Thousand Oaks, CA (US); William K. Arnold, Woodland Hills, CA (US)

(73) Assignee: Royce Medical Company, Camarillo, CA (US)

( * ) Notice: Subject to any disclaimer, the term of this patent is extended or adjusted under 35 U.S.C. 154(b) by 0 days.

(21) Appl. No.: 09/857,396

(22) PCT Filed: Aug. 29, 1997

(86) PCT No.: PCT/US97/15265

§ 371 (c)(1),
(2), (4) Date: May 31, 2001

(87) PCT Pub. No.: WO98/08470

PCT Pub. Date: Mar. 5, 1998

Related U.S. Application Data

(63) Continuation-in-part of application No. 08/705,218, filed on Aug. 29, 1996, now abandoned.

(51) Int. Cl.
*A61F 5/00* (2006.01)
*A61F 5/37* (2006.01)

(52) U.S. Cl. .............................. 602/27; 602/5; 602/23; 128/882

(58) Field of Classification Search ............... 602/5, 602/14, 23, 27, 62, 65; 129/882; 2/16, 22, 2/455; 36/89, 90, 140
See application file for complete search history.

(56) References Cited

U.S. PATENT DOCUMENTS

| 2,818,571 | A | 1/1958 | Grant |
| 4,730,610 | A | 3/1988 | Graebe |
| 4,966,134 | A | 10/1990 | Brewer |
| 4,977,891 | A | 12/1990 | Grim |
| 5,007,111 | A | 4/1991 | Adams |
| 5,007,416 | A | 4/1991 | Burns et al. |

(Continued)

OTHER PUBLICATIONS

International Search Report and International Preliminary Examination Report for International Application PCT/US97/15265.

*Primary Examiner*—Gregory L. Huson
*Assistant Examiner*—Fenn C. Mathew
(74) *Attorney, Agent, or Firm*—Fulwider Patton Lee & Utecht, LLP

(57) ABSTRACT

An ankle support (100) is constructed using a molded pad (110) and a rigid shell (112). The pad (110) and the shell (112) may be sealed together to form a bladder-pad cushion for comfort. The internal structure of the pad (110) is molded to include geometrically shaped cells of various size, shape and thickness to provide differing levels of localized comfort to the user of the ankle support (100). The pad may be made from a thermoplastic elastomer (TPE) which is spring-like and resists compression sets. The pad may include integrally-molded fingers extending to the shell. The fingers may have different lengths in one or more regions, in order to increase the cushioning effect in a particular region. The pad/shell combination may form a sealed bladder, and a pneumatic pump may be provided in conjunction with the shell so that the user can inflate the bladder.

37 Claims, 10 Drawing Sheets

U.S. PATENT DOCUMENTS

| | | | |
|---|---|---|---|
| 5,233,767 A * | 8/1993 | Kramer ......................... 36/28 |
| 5,288,286 A | 2/1994 | Davis |
| 5,366,439 A | 11/1994 | Peters |
| 5,403,265 A | 4/1995 | Berguer et al. |
| 5,445,602 A | 8/1995 | Grim et al. |
| 5,496,610 A | 3/1996 | Landi et al. |

* cited by examiner

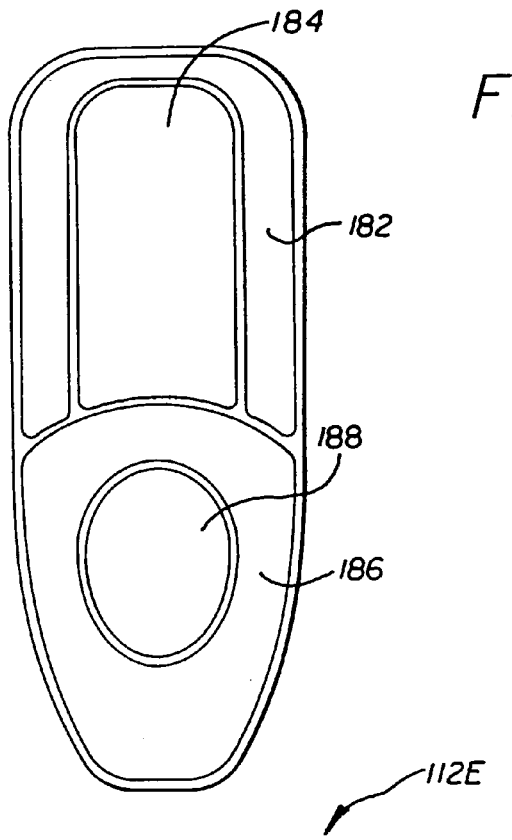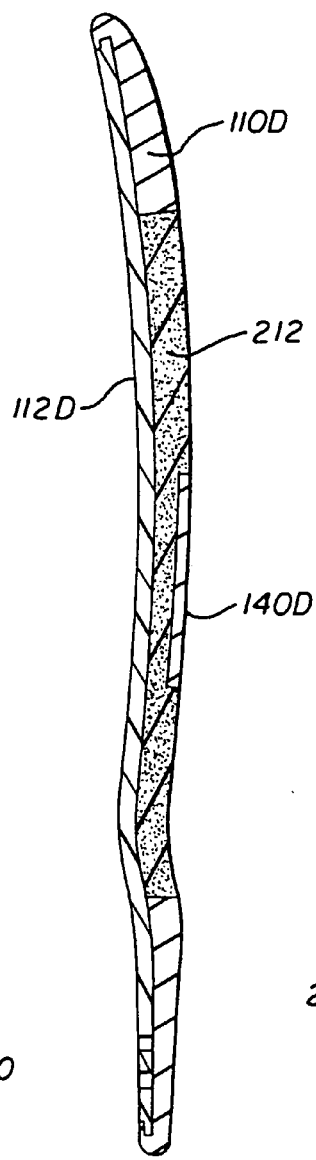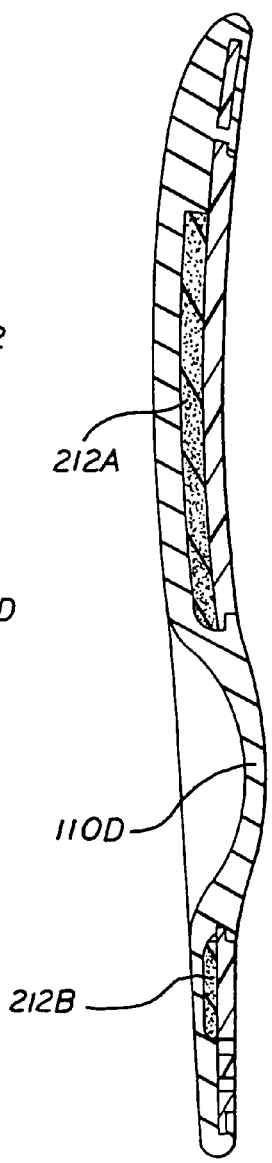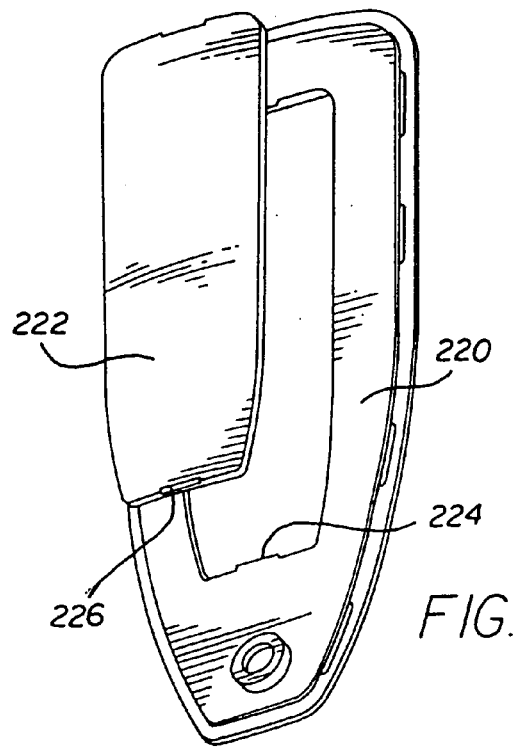

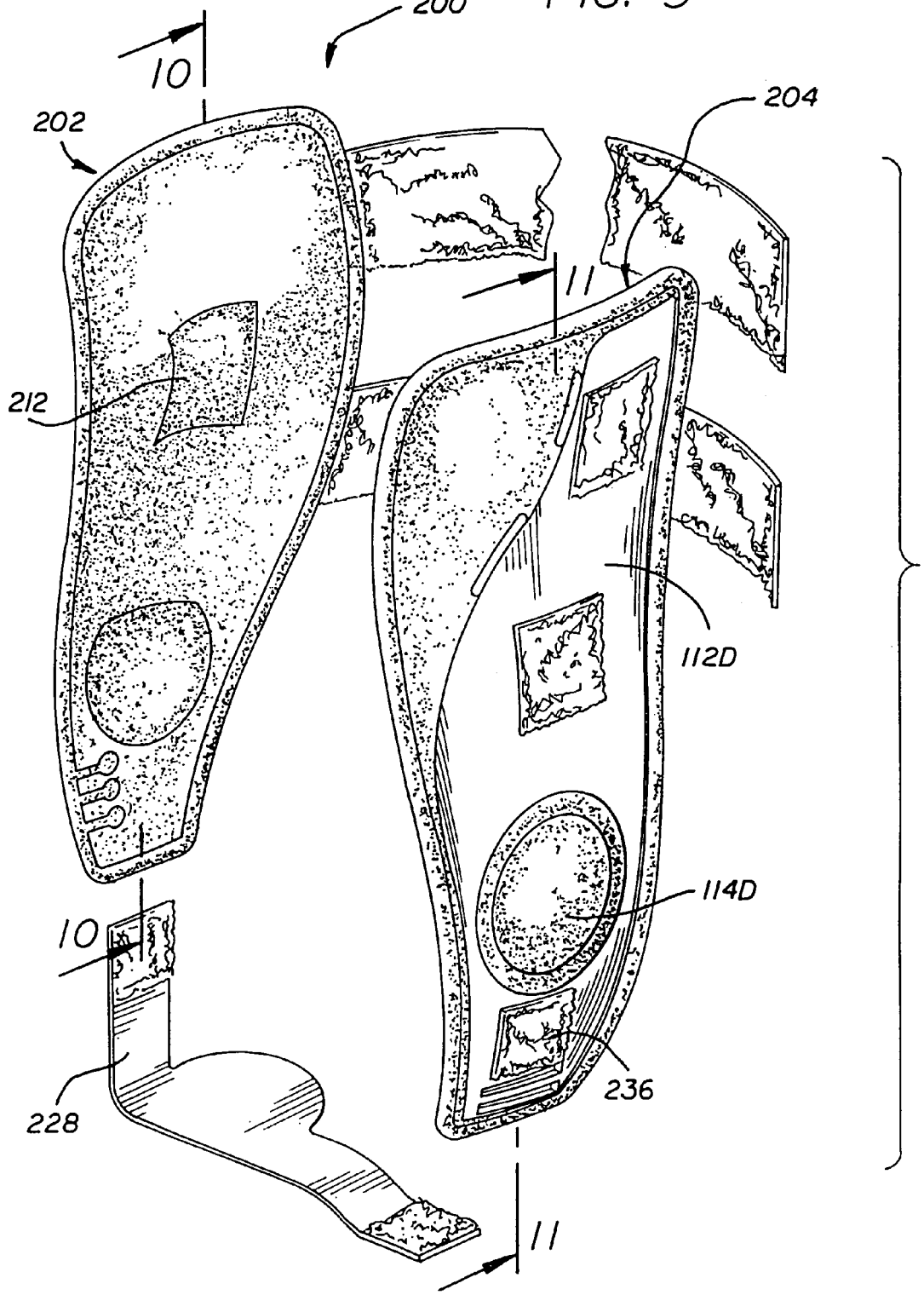

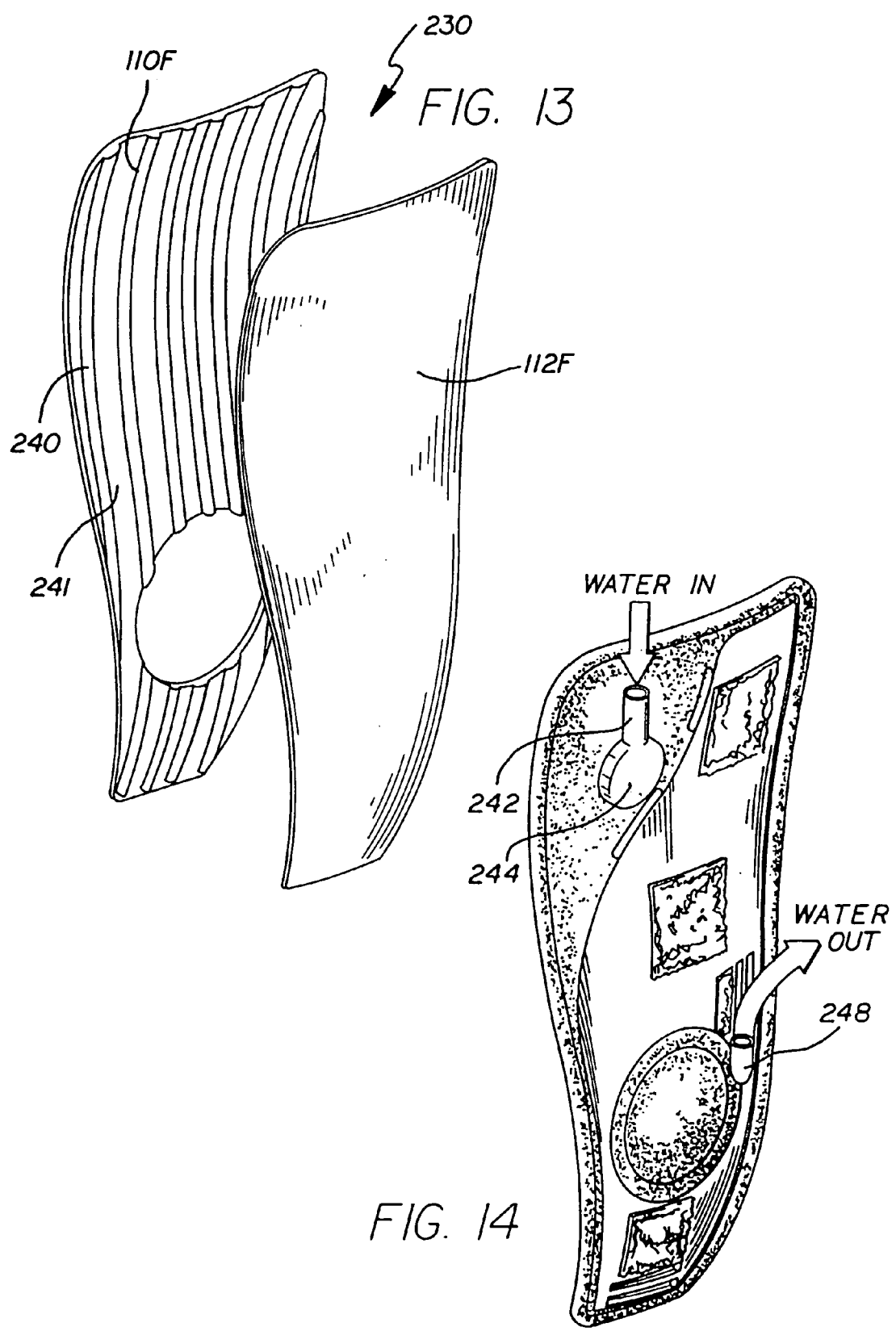

COMFORTABLE ORTHOPAEDIC SUPPORT AND THE METHOD OF MAKING THE SAME

RELATED APPLICATION

The present application is a continuation-in-part of U.S. patent application Ser. No. 08/705,218, now abandoned, which was filed on Aug. 29, 1996 and which is incorporated by reference herein.

BACKGROUND OF THE INVENTION

1. Field of the Invention

The present invention generally relates to an improved orthopaedic device, and specifically to a orthopaedic support for body limbs or joints with emphasis on the construction of the support for comfort fit.

2. Description of Related Art

A variety of orthopaedic supports have been proposed to provide cushioned support to the limb, and most typically to an ankle and the lower leg after an injury. Typically, these ankle supports offer a rigid or a semi-rigid shell for sturdy support with padding for comfort. The padding material typically comprises foam, bladder, or other cushioning material. For example, in the U.S. Pat. No. 4,628,945, granted Dec. 16, 1986 to Glenn W. Johnson Jr., and entitled "Inflatable Ankle Brace with Porous Compressible Filler," an ankle brace comprising a rigid outer shell with an air-inflatable, bladder type liner is described. In that patent, the support is provided by the outer shells and the comfort is provided by the air-inflatable liner. Another design for an ankle brace is disclosed by the U.S. Pat. No. 5,348,530 granted on Sep. 20, 1994, also granted to Tracy E. Grim, William K. Arnold, and Joseph M. Iglesias and entitled "Pneumatic Ankle Brace with Bladder and Pump Arrangement." The '530 patent discloses an ankle brace design with rigid side supports and pneumatic bladder to serve as the cushioning material between the side supports and the wearer's leg.

Although these patents and others describe the padding materials used to improve the comfort to the person wearing the orthopaedic support, none of the previous designs suggest the provision in a single structure of different levels of support in different local regions of the limb being supported by the support.

U.S. Pat. No. 5,366,439 to Peters discloses a pad made from several sheets of material, forming closed cells of pressurized air. The cells are all of uniform size and shape and do not provide specialized local support at distinct points on the ankle. The cells must be closed and filled with pressurized air, because otherwise the pad would not provide any support.

SUMMARY OF THE INVENTION

As an improvement over the prior designs, the present invention discloses a new design for supporting limbs. In this specification, the inventive design will be exemplified in ankle supports. The ankle support of the present invention provides for a creative way of forming and utilizing injection-molded resilient material, preferably thermoplastic elastomer (TPE) pads, to provide a light weight, durable padding while allowing for varying the degree of localized cushioning for different areas of the ankle support. Utilizing the injection molding technology, the resilient pads may be contoured and shaped to highly detailed designs. In addition to the varying the degree of localized support and cushioning, the orthopaedic support of the present invention may be used to provide the ideal levels of compression to the portions of the limb being supported.

An orthopaedic support for comfortably supporting a limb is disclosed in the present specification. As a typical application of the orthopaedic support, an ankle support will be discussed in this specification. The ankle support includes a outer shell formed for fitting about the limb, such as the lower leg, and a pad. A molded thermoplastic elastomer (TPE) pad is placed in between the outer shell and leg. The shell and the pad may be secured together by various means including infra-red welding, induction welding, bonding using adhesives, snap fitting, or overmolding. The pad is preferably made of molded TPE material and has molded structure to provide differing levels of cushioning support for the wearer of the orthopaedic support.

The rigid shell of the ankle support may be formed to accommodate the malleolus or ankle bone when fitted on the user. Alternatively, the shell may be configured to surround but not cover the area around the malleolus. In that case, only the resilient padding may be configured to cover the malleolus.

The pad is welded on the shell or attached using other suitable methods. Alternatively, an overmold may be used to attach and may seal the resilient padding to the shell. The overmold may be of same material as the padding. If an overmold is used, the securing is accomplished by molding the overmold material at least around the edges of the ankle support. If the overmold material is the same material as the pad, then the overmold may be a mere extension of the pad and the boundary between the pad and the overmold may not be distinguishable.

Instead of using an overmold to seal the pad onto the shell, the pad, having at least one smooth, continuous side, may be welded directly onto the shell to seal the assembly.

A liner may be provided to cover the pad. The liner may be of a material such as cloth or other moisture absorbing material for more comfortable engagement with the skin of the user.

Typically, the TPE pad comprises a substantially continuous smooth side, and an opposing side with molded protrusions or cells. The TPE pad is then sealed to the shell with the opposing side having the protrusions or cells facing the shell. If the seal is an air-tight seal, the shell-pad seal defines a bladder. Alternatively, the TPE pad itself may be configured as a bladder with cell structures built inside the bladder. This may be accomplished by placing a film of similar material on the open side of the cells and sealed around the outside to create a bladder, using the cells to prevent bottoming out during use. Alternatively, the molded pad provided with cells may be placed between two layers of air/fluid impervious film that are sealed around their periphery. In any case, the protrusions built within the interior of the TPE pad, which may be domes, cylinders, or other regularly or irregularly shaped protrusions, define the interior space of the ankle support and provides for differing levels of localized cushioning determined by the shape, size, and density of the protrusions, or cells, as well as the thickness of the walls of the cells. If the protrusions are shaped to define geometric areas such as rectangles, cylinders, etc., then each of the protrusions may be called a cell. The cell structure, defining the internal structure of the bladder, will be further discussed in the "Detail Description of the Preferred Embodiment(s)" section below.

To secure the orthopaedic support to the ankle and the lower leg, straps, buckles, or other suitable devices may be attached to the supports. Also, a heel strap, attached near the bottom of each of the ankle pads, connects the ankle supports to each other. The heel straps are adjustable to fit the size of the wearer of the ankle support.

In accordance with one broad aspect of the invention, a pair of ankle supports for comfortably supporting the ankle are formed to conform to the shape of the ankle and the lower leg, and includes, for each of the supports, a shell and a resilient, preferably TPE pad for cushion. The pad includes molded geometric shaped cells within the pad to provide differing levels of localized cushioning.

In accordance with another broad aspect of the present invention, an orthopaedic support bladder pad is formed out of thermoplastic elastomer (TPE). The bladder pad is injection molded to include a space within its interior.

The space interior to the bladder pad may be filled with trapped air, or foam material, or geometric shaped cell structures made of the TPE material to provide differing levels of localized cushioning. The geometrically shaped cells may be interconnected via molded channels to allow air and/or fluid to pass between the cells.

The present invention also discloses a new method of manufacturing the comfortable ankle support. In accordance with a broad aspect of the present invention, the comfortable ankle support may be manufactured by forming a rigid shell for fitting about the lower leg, placing a resilient pad against the shell, and welding or otherwise bonding the resilient pad to the shell. The resilient material used for the padding is typically a thermoplastic elastomer (TPE); however, the resilient material may be other than the TPE such as gels, thermoplastic urethane (tpu), thermoplastic rubber (tpr), two part urethanes, or foams, and the resilient material may be secured to the shell by overmolding with either a rubber or a plastic compound.

The orthopaedic support may include a heel bladder, connected to the side pads for providing varying pressures applied to the lower leg, as the patient walks.

In an alternative embodiment, the support may be provided with fingers that extend from the support to the ankle in order to provide cushioning to the ankle. The fingers may be of uniform length, or may have different lengths in different regions of the support. The fingers may be arranged at predetermined locations about the periphery of individual cells. The corresponding cells may be of different shapes in different regions. The length of the fingers and the shapes of the cells may be adjusted to customize the comfort and padding of the support in particular regions.

In a further alternative embodiment, the overmold may be molded about the edges of the shell rather than about the edges of the pad. The overmold may also be provided with a ridge that extends about the periphery of the overmold on the interior side of the shell, for bonding the pad onto the overmold.

Other aspects, features, and advantages of the present invention will be apparent to those persons having ordinary skill in the art to which the present invention relates from the foregoing description and the accompanying drawings.

BRIEF DESCRIPTION OF THE DRAWINGS

FIG. 8 illustrates the areas of the ankle support which may require differing levels of cushioning and support;

FIG. 9 is a diagrammatic, perspective view of an alternative embodiment of the ankle support of the present invention employing foam material for cushioning;

FIG. 10 is a cross-sectional side view illustrating the ankle support pad structure, taken along lines 10—10 of FIG. 9;

FIG. 11 is a cross-sectional side view illustrating the ankle support pad structure of an alternative embodiment;

FIG. 12 illustrates an alternative embodiment of the shell with a removable core for varying the rigidity of the shell;

FIG. 13 illustrates an alternative embodiment of the ankle support and pad in which a channeled pad is employed;

FIG. 14 illustrates inlet and outlet ports and valves of an ankle support useful for hot and/or cold therapy.

DETAILED DESCRIPTION OF THE PREFERRED EMBODIMENT(S)

Figure 1:
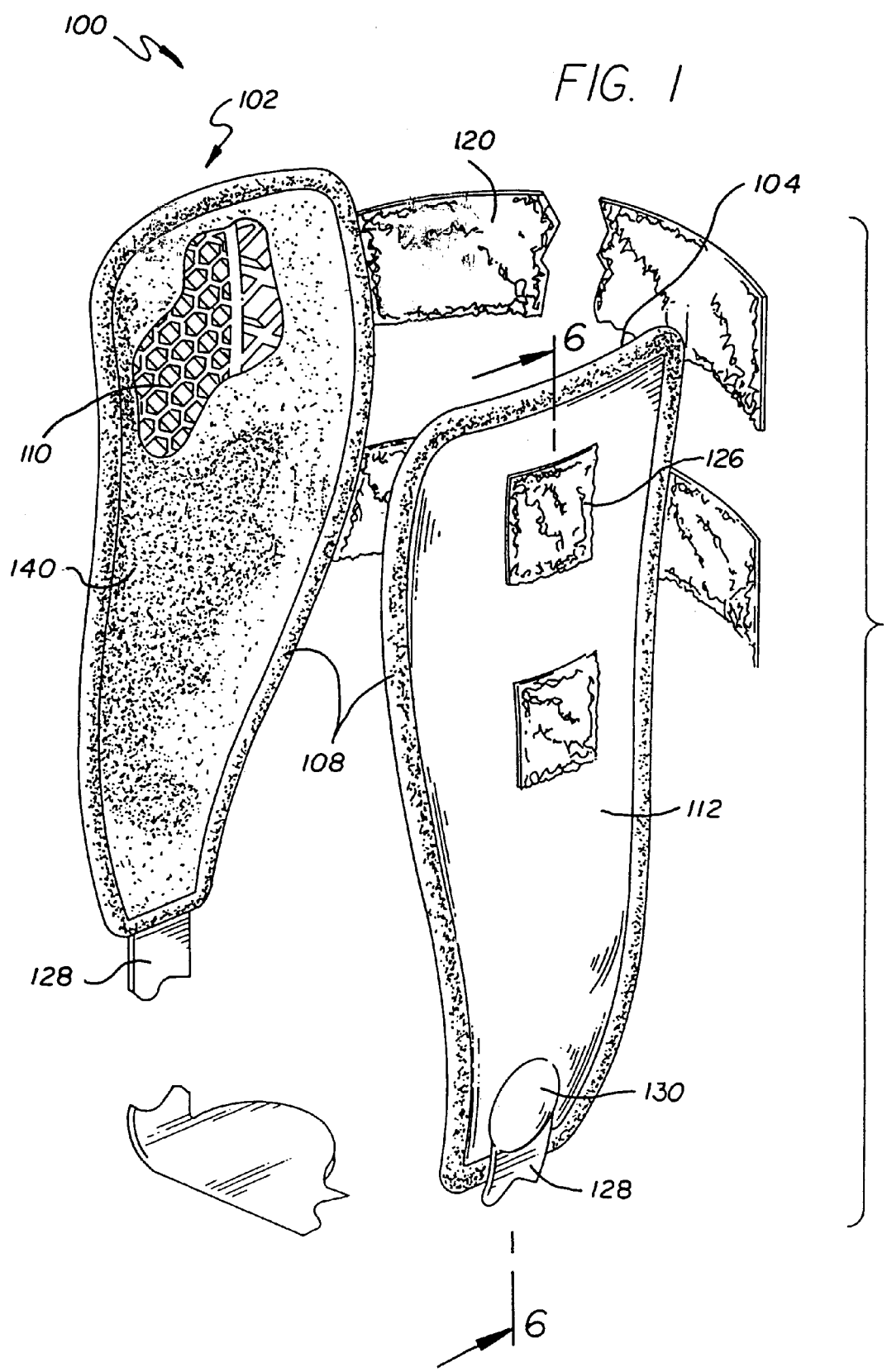
FIG. 1 is a diagrammatic, perspective view of a comfortable orthopaedic support as exemplified by comfortable ankle supports illustrating the present invention.

Referring to the drawings, particularly to FIG. 1, a comfortable orthopaedic support 100 is shown. As a preferred embodiment of the present invention, and to facilitate the description of the present invention, this section of the document will discuss comfortable ankle supports. However, comfortable orthopaedic supports in accordance with the present invention may be manufactured for and applied to other parts of the body.

FIG. 1 illustrates an ankle brace including an ankle support 102 for the medial side of the lower leg and a cooperative ankle support 104 for the lateral side of the lower leg. However, because the ankle support design of the present invention is applicable for either one or both sides of the lower leg, the following discussions will not differentiate between the medial and the lateral side supports. The ankle support comprises a rigid outer support, or a shell, 112, and a thermoplastic elastomer (TPE) pad 110. The shell 112 and the pad 110 may be welded together or may be sealed together by an overmold 108 at least around the edges. The overmold 108 may be an extension of the TPE pad 110 and made of the same TPE material as the pad 110. A flexible layer 140 is preferably integral with pad 110, but may be separate and bonded thereto. The rigid side support 112 may be shaped to accommodate the ankle or the malleolus area. The TPE pad 110 has an inner structure as shown by the cut-away area to various geometric shapes to provide differing levels of localized comfort. The interior design of the pad 110 will be further illustrated by the following figures and the corresponding discussions below. A heel strap 128 is attached to the lower portions of both of the ankle supports by a cap 130.

The comfortable ankle support may be secured onto the lower leg using fastening fabric, such as the hook and loop type fastening material sold under the trade name VELCRO®, straps and buckles, or any other suitable means. FIG. 1 illustrates the use of the loop-type VELCRO® straps 120 along with the hook-type VELCRO® sections 126 attached to the shell 112 as the means of securing the ankle supports to the lower leg.

Although the preferred embodiment of the present invention as disclosed as being implemented using a pair of rigid side supports, the pad 110 may be used as the cushioning member for a unitary ankle support such as the "Adjustable Tension Ankle Support" disclosed by U.S. Pat. No. 4,869,267 issued to Tracy E. Grim and Thomas M. Smario.

Figure 2:
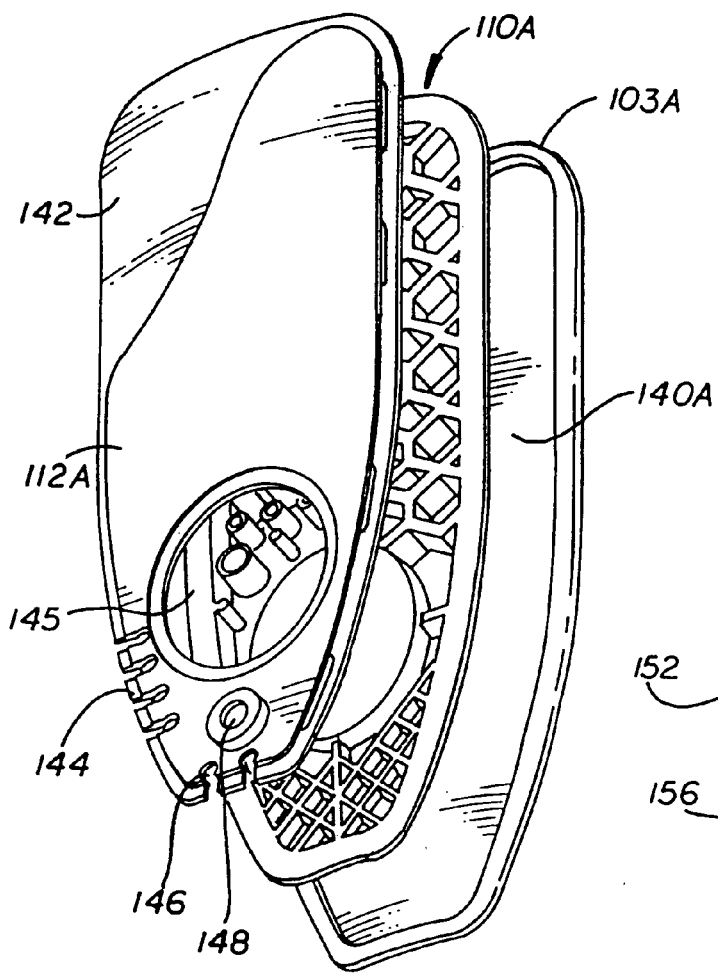
FIG. 2 is an exploded view of the ankle support shown in FIG. 1, and illustrating the construction of the ankle support.

FIG. 2 is an exploded view of an ankle support illustrating the construction of the ankle support and its internal structure. Incidentally, FIG. 2 is shown flat for convenience and clarity in showing the internal construction, but would actually be curved and contoured to the general shape of the ankle as shown in FIG. 1. FIGS. 3, 4, 8 and 12 have also been illustrated as being flat, but would actually be curved in configuration. Returning to FIG. 2, the shell 112a as illustrated may be partially covered by the TPE material 142 which may be an extension of the overmold 108a which may also cover the TPE pad 110a. The pad 110a is placed in between the outer support, or rigid shell, 112a and the inner liner 140a. The liner 140a may be of same TPE material as the pad 110a or other suitable materials such as cloth, neoprene, etc. Alternatively, the liner 140a may not be necessary if the pad 110a has a substantially continuous skin on the side of the pad upon which the liner is expected to attach to. The overmold 108a may comprise the resilient material which seals the shell 112a to the pad 110a. The inner cell structure of the TPE pad will be illustrated in detail by FIGS. 3 and 4 and described by the corresponding discussions below. If the pad 110a is welded to the shell 112a, the overmold 108a may not be a necessary element of the ankle support.

The rigid outer support, or the shell, 112a may be formed of relatively stiff or semi-rigid plastic, and may include cutouts 144 and 146 which serve to increase the shell's flexibility near the malleolus area 145 to increase the comfort and to decrease the chance of the shell 112a digging into the often sensitive ankle region. The cutouts 144, 146 may be implemented on any portion of the shell 112a to increase the flexibility of the shell 112a for the area. A receptacle 148 is provided near the bottom of the shell 112a to allow the attachment of the heel strap 128 of FIG. 1 by welding, snap-fit with a retention cap, rivet, or other suitable attaching means.

The liner 140a of the ankle support is substantially smooth. The overmold 108a as utilized substantially covers at least the outer edges of the TPE pad 110a, the liner 140a, and the shell 112a forming an air-tight seal and trapping air.

Again, if the pad 110a is welded or bonded onto the shell 112a and if the pad 110a includes a substantially continuous surface (for the side away from the shell), then the liner 140a and the overmold 108a are not necessary elements of the ankle support.

In the embodiment as shown by FIG. 2, the shell 112a surrounds but does not cover the malleolus or protruding portion of the ankle, allowing the malleolus to extend into the ankle support. That area is covered only by the outer surface of the TPE pad 110a or the liner 140a.

In an alternative embodiment, the shell itself includes the overmold about its edges. A pad is molded separately, and the edge of the pad is bonded to the overmold The liner 140a would either be molded with the lip, or would be a separate material onto which the lip 108a is molded.

Figure 3:
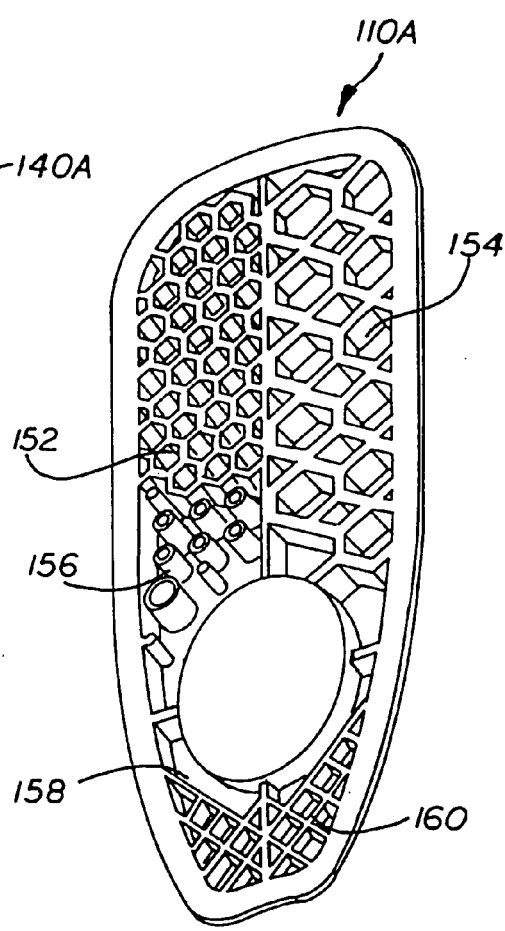
FIG. 3 is a perspective detailed view of the internal cell structure of the thermoplastic elastomer (TPE) pad illustrated by FIG. 2.

FIG. 3 provides a detailed perspective view of the interior design of the TPE pad 110a. The TPE pad 110a is injection molded to include various protrusions or cells. These cells may be molded as domes, pyramidal or other regularly or irregularly shaped geometrical protrusions. The embodiment as illustrated by FIG. 3 includes various sized hexagonal cells resembling honeycomb structures 152 and 154, cylindrical cells 156, criss-cross or checkered-patterned cells 160, and irregularly shaped cells 158. The size, shape, and density of the cells as well as the thickness of the walls defining the cells determine the level of cushioning for the local areas of the ankle support.

The utilization of the injection molded TPE material for orthopaedic supports has many advantages. First, the TPE pad can be molded to include detailed designs such as geometrically shaped cells. The TPE pad can be specifically contoured to the malleolus areas, the calf, and the calcaneal regions of the support. Although the TPE material is more dense than other padding materials such as foam, the innovative design including molded cell-structure as illustrated by FIGS. 2–7 overcomes this disadvantage by reducing the weight of the product. The reduction in the weight of the pad also translates into lower cost and increased value to the end user of the product.

One suitable thermoplastic elastomer (TPE), is available under the name RIMFLEX, made from KRATON® Polymer. It is produced by Shell Oil Company and is available from Synthetic Rubber Technologies of Uniontown, Ohio. There are many other sources of thermoplastic elastomers. The material may be molded by any of the numerous injection-molding companies across the nation. Other material may be used in place of the TPE, including thermosetting and thermoplastic materials.

Figure 4:
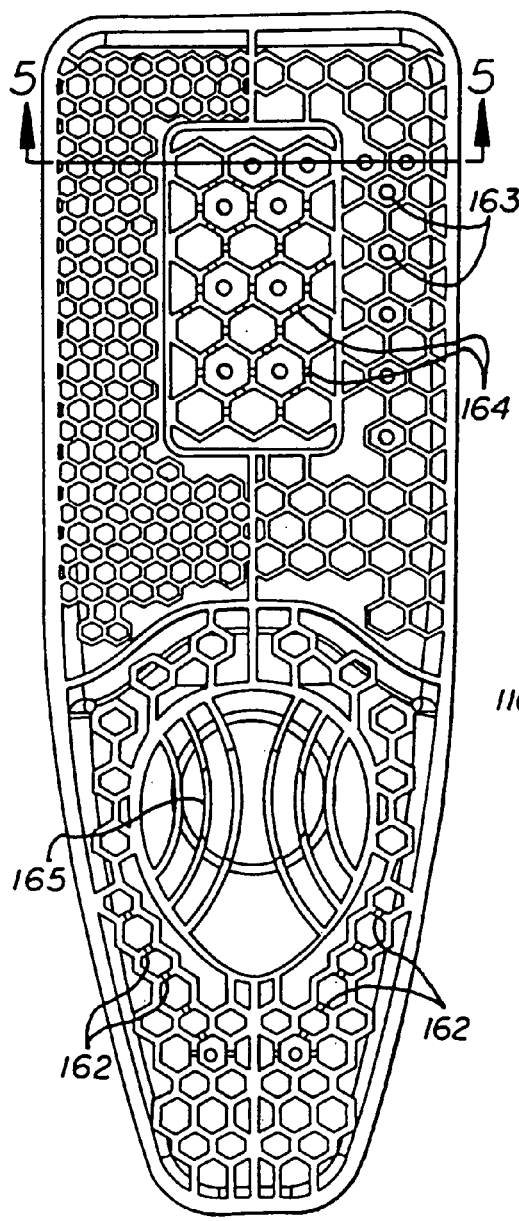
FIG. 4 illustrates various internal geometric shaped cells and channels of the TPE pad.

Continuing to refer to FIG. 3 but also referring to FIG. 4, the geometrically shaped cells of the pad 110 may be interconnected via channels 162 and 164 as illustrated by FIG. 4. The figure illustrates channels 162, molded between the cells of the TPE pad 110a to allow passage of air or fluids amount the cells of the pad 110a. The channels provide the means for the movement of the air or fluids between the cells, creating a massaging effect on the lower leg, thereby promoting blood flow. Also, the channels may be designed in a manner in which external fluid may be circulated with the ankle pad for hot and cold therapies.

FIG. 4 also illustrates the fact that the cells of the pad 110a may be molded to include shapes such as logos and trademarks as well as geometrical shapes as indicated by reference number 165.

Figure 5:
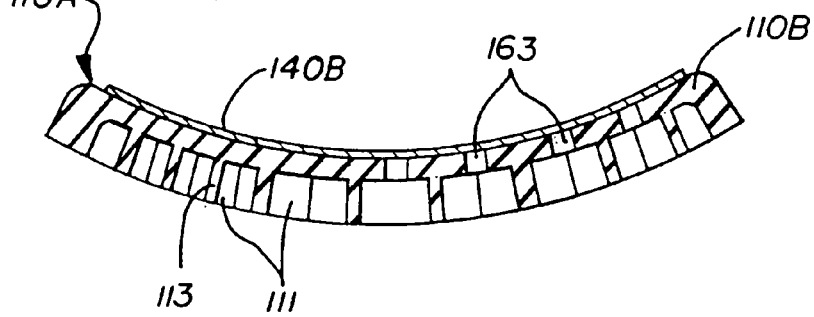
FIG. 5 is a partial transverse cross-sectional view of the pad shown in FIG. 4 taken along lines 5—5 of FIG. 4.

FIG. 5 is a partial transverse cross-sectional view of the TPE pad embodiment as shown in FIG. 4 taken along the line 5—5. The geometric cells 111 are defined by its walls 113. In the embodiment as shown, the pad 110a includes a smooth, substantially continuous side 110b eliminating the need for a liner 140 of FIG. 2 for this embodiment. However, even though not required, a liner 140b still may be used to increase comfort.

FIGS. 4 and 5 also illustrate that the cells of the pad 110a may include openings 163 on its smooth side allowing air to pass in and out of the pad to relieve pressure. If the liner 140b is made of cloth or other breathable material, the openings 163 do not have to extend through the liner 140b.

Figure 6:
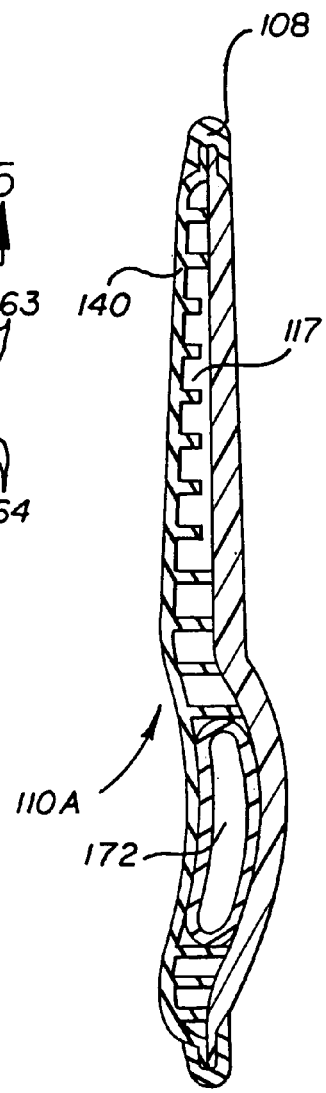
FIG. 6 is a cross-sectional side view illustrating the structure of one alternative embodiment of the ankle support shown in FIG. 1, taken along lines 6—6 of FIG. 1.
Figure 7:
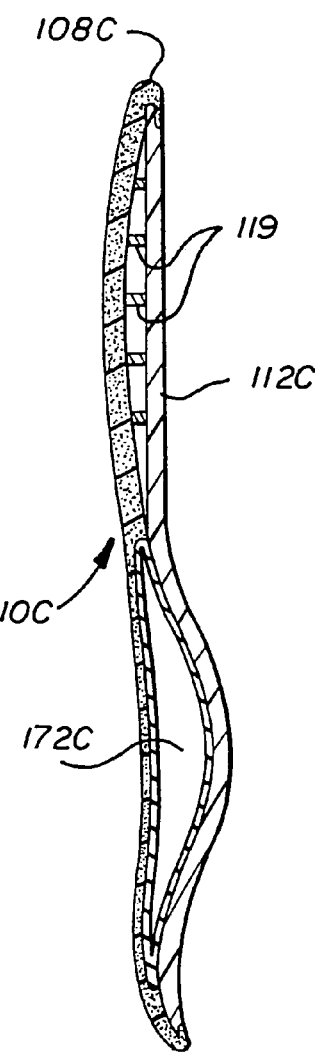
FIG. 7 is an cross-sectional side view of an alternative embodiment of an ankle support.

Referring now to FIGS. 6 and 7, cross-sectional side views illustrating the internal structure of the ankle supports of FIG. 1 are illustrated. Referring specifically to FIG. 6, a cross-sectional side view of the ankle support is illustrated. The shell 112 provides rigid or semi-rigid support for the ankle support and the TPE pad 110 provides the cushioning for the ankle support. The TPE pad 110 includes geometrically shaped cell structures. The overmold 108 may seal the TPE pad 110 and the liner 140 to the shell 112. If the seal is an air-tight seal, and the liner 140 (which is an integral part of the pad 110) includes no openings as illustrated by the reference number 163 of FIG. 4, then a bladder is formed. In the embodiment as shown, the shell 112 covers the entire lower leg including the malleolar area. Also, the TPE pad 110 may include a smaller, internal bladder 172 around the malleolus area providing additional level of cushioning. Alternatively, instead of a bladder 172, the additional cushioning may be provided by inserting other soft material in the space such as open cell foam material or gels.

Reference number 117 shows that the structures for the pad 110 may be formed such that the TPE material does not span the entire distance from the liner 140 to the shell 112 creating a pressure free travel of the padding 110 to the shell 112. The pressure free travel design provides for unsurpassed softness and comfort for the area of the pad. This technique allows additional air to be trapped under the pad 110 and creates additional room for the pad 110 to flex for softer cushioning. Also, the reduction in the amount of material used for the pad 110 leads to a lighter ankle support and reduced production costs.

An alternative embodiment of the ankle support is illustrated by FIG. 7. Similar to the ankle support as shown by FIG. 6, the shell 112c and the TPE pad 110c are sealed to each other by an overmold 108c substantially molding at least the edges of the shell 112c and the pad 110c. However, unlike the embodiment of FIG. 6, the pad 110c of FIG. 7 does not include internal geometric structures for cushioning. The pad 110c includes only an internal bladder 172c around the malleolus area.

In the embodiment of the present invention as illustrated by FIG. 7, the cushioning is provided by internal structures molded directly onto the shell 112c as illustrated by reference number 119. In this embodiment, the cell structures for the padding, such as the geometric configurations shown in other figures, has been initially molded directly on the shell 112c. Subsequently, the layer 108c is bonded to the shell 112c around the edges of the shell, leaving the open spaces defined by the molded cell structures 119.

Utilizing the geometrically shaped cells molded onto the TPE pad, the ankle supports 102, 104 of FIG. 1 may provide differing levels of cushioning to the different areas of the lower leg being protected by the ankle support. FIG. 8 illustrates one possible map of the areas of the ankle support which may require different levels of cushioning. For instance, the malleolus area 188 may require very soft support using a configuration indicated by reference number 117 of FIG. 6 or could be provided by an internal bladder-type structure 172c as shown in FIG. 7. Using the construction shown at 117 in FIG. 6 would allow some distance for free travel, with increasing resistance, and protection against bottoming out. The area 186 surrounding the malleolus may require a soft cushioning, slightly firmer than the area 188, to avoid aggravation of an injured malleolus. The area 184 supporting the lower tibia may require firm support and its surrounding area 182 may require softer cushioning for comfort. The softer cushioning around the edges of the support prevents the edges of the shell from digging into the wearer's leg. As already indicated, the degree of cushioning of these areas may be predetermined. Other mapping schemes may be used to support the ankle region or to support other limbs of the body.

An alternative embodiment of the orthopaedic support 200 is illustrated by FIG. 9. The ankle supports 202 and 204 of this embodiment of the orthopaedic support 200 include other cushioning materials in addition to TPE pads as described above. The additional cushioning may be provided by the embedded cushioning material 212. Typically, the material used for the embedded cushioning is foam or gels. Because the TPE material is more durable (tear-resistant), flexible, water resistant, and hypo-allergenic than foam material, it makes a better padding for ankle supports. However, because of its higher density, it may not provide cushioning which is as soft as may be desired, and could involve some increase in weight. Using the design illustrated by FIG. 9, the benefits of the TPE pad may be retained while gaining the additional cushioning and reduction in weight, provided by the foam core 212.

In short, FIGS. 1–8 illustrate an embodiment of the ankle support of the present invention where the padding for the support is created using injection molded TPE pads with internal geometrically shaped cells. Alternatively, FIGS. 9–11 illustrate an embodiment of the ankle support of the present invention where the padding for the support is created using a molded TPE pad with a cushioning core of a different material.

Also illustrated by FIG. 9 is the adjustable heel strap 228 which may be detachably mounted to the ankle supports using the loop and hook type mounting member 236 which, in turn can be affixed to the lower portion of the ankle supports permanently or by a snap-on unit or other suitable attaching means.

The shell 112d of the ankle support 202, 204 may be formed to surround but not cover the malleolus area 114d, with the trampoline cushioning effect resulting from the lack of rigid coverage in the malleolus area allowing less padding in that area.

Referring to FIGS. 10 and 11, cross-sectional side views illustrating the ankle support pad structure, taken along lines 10—10 of FIG. 9 is shown. The foam pad 212 is embedded in the TPE pad 110d between the shell 112d and the outer surface 140d of the TPE pad 110d. This construction increases the cushioning of the TPE pad 110d while maintaining the water resistance, durability, and other favorable characteristics of the TPE pad.

Alternatively, for the cross section of the ankle support as illustrated by FIG. 11, the embedded foam pad 212a, 212b does not cover the malleolus area. Rather, the foam pad surrounds the malleolus area as indicated by 212a and 212b. As illustrated by FIG. 11, only a layer of the TPE pad 110d covers the malleolus area. This creates a "trampoline" type effect. The malleolus, as illustrated by the figure, is covered by a TPE "trampoline," which provides a flexible padding without the rigid shell. The foam pad 212a and 212b of may be replaced by gel because, unlike the design illustrated by FIG. 10, the space defined 212a and 212b is completely enclosed by the TPE over pad 110d.

FIG. 12 illustrates an adjustable shell design applicable to the present type of ankle support. The shell 112e may comprise a rigid or semi-rigid plastic shell frame 220 and a shell core 222 which may be removable. The removable shell core 222 may be replaced with more or less rigid shell cores as the needs of the patient change over time. The initial shell core 222 may be of a very rigid material so that prevention of inversion or eversion is greatest, thereby allowing the patient to regain stability in his or her ankle. Once the ankle has healed and the patient is ready for more demanding forms of exercise, the shell core 222 may be changed to a less rigid material so as to allow further movements of the ankle. Further, the shell core 222 may be removed entirely for further flexion, if desired. In the embodiment as illustrated by FIG. 12, the shell core 222 fits snugly into the shell frame 220, and snaps into place. The snapping action is accomplished using a protrusion 224 and the indentation 226.

The arrangement of FIG. 12 can also be employed as a "trainer" style ankle support to prevent injury to an ankle that has healed somewhat but which requires protection from reinjury. In the "trainer" embodiment, the outer shell 220 is made from a flexible material such as a low density polyethylene or polypropylene. An insert 222 may be made from a material that is more rigid than the flexible outer shell 220, such as high density polyethylene, steel, nylon and other rigid materials.

In the preferred embodiment that FIG. 12 illustrates, the insert 222 snaps into place on the shell 220. However, the insert may alternatively be secured to the shell 220 in other ways, such by rivetting, with adhesive, or by welding into place. An advatage of this arrangement is that the insert 222 may be secured into place immediately after the ankle is injured. However, after the ankle has healed somewhat, the insert 222 may be removed from the outer shell 220, making the support more flexible and allowing the person wearing the support to engage in a wider variety of activities.

Yet another alternative embodiment of the ankle support is illustrated by FIGS. 13 and 14. Referring to FIG. 13, the ankle support 230 is illustrated with a shell 112f and the TPE pad 110f with molded tubular channels 240 and grooves 241 as its inner surface. Such design is particularly useful for hot and cold treatments of the ankle and the lower leg. FIG. 14 illustrates a water intake port 242 and an intake valve 244 and a water outlet port and an outlet valve 248.

Figure 15:
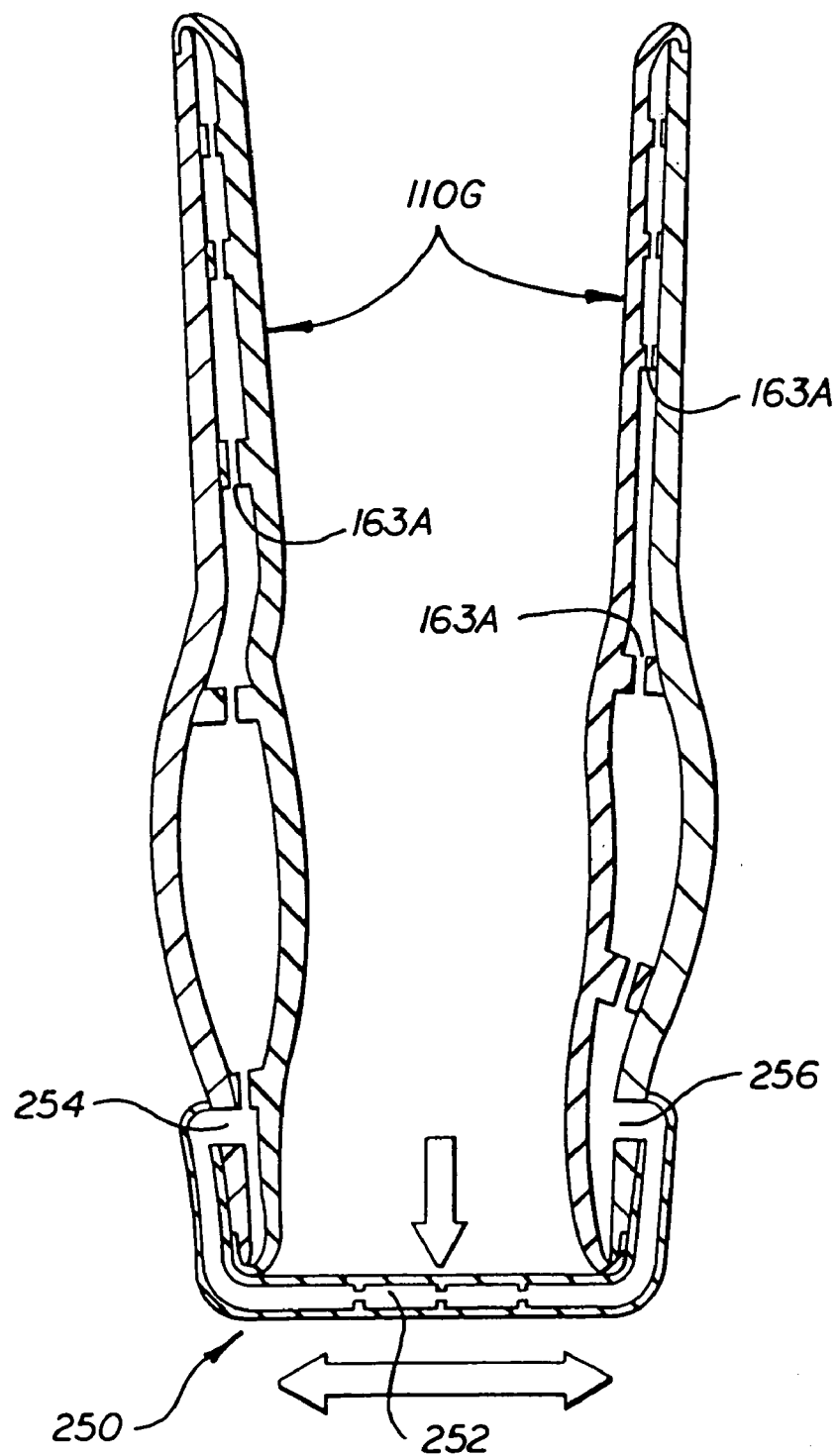
FIG. 15 is a cross-sectional view of another embodiment of the present invention.
Figure 16:
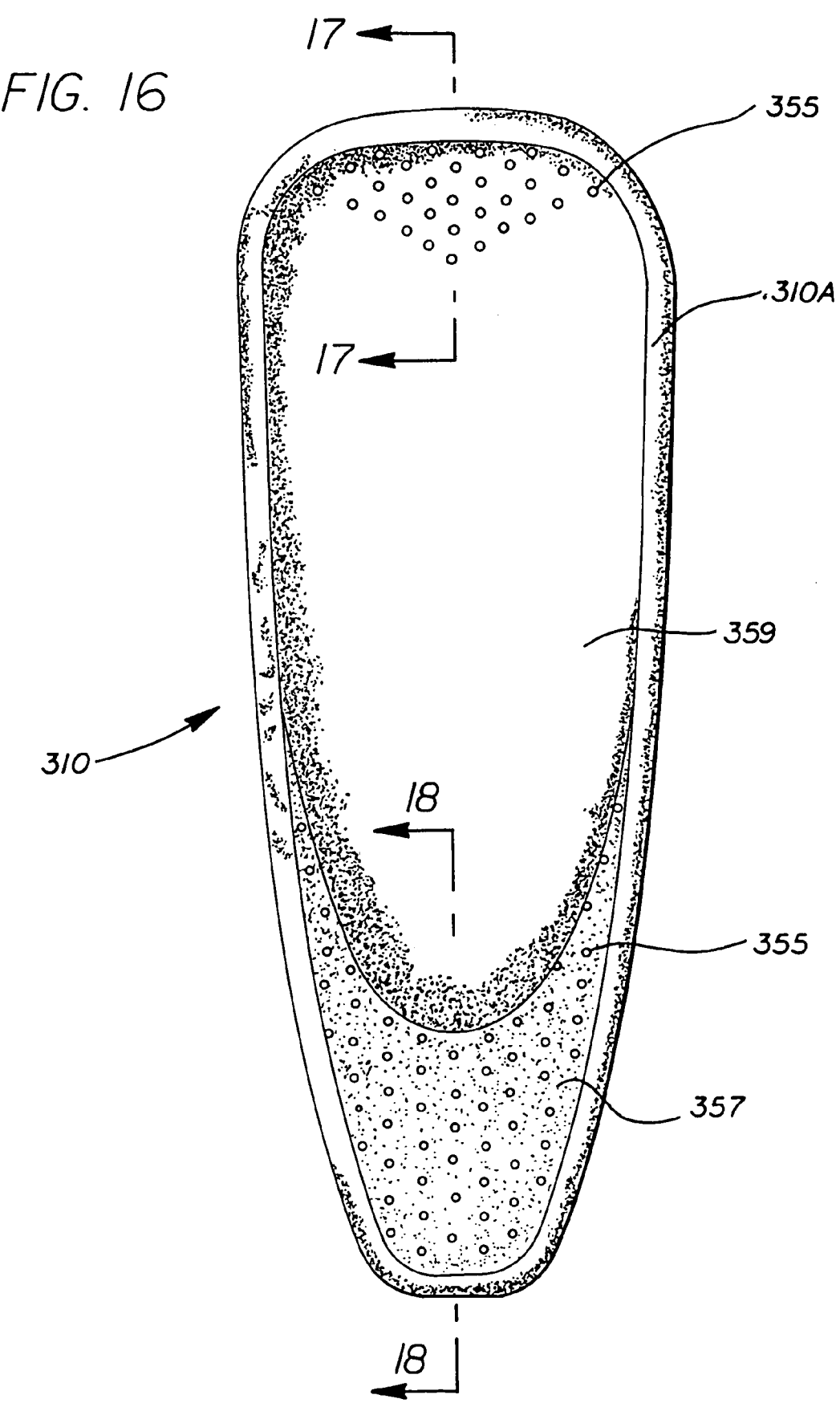
FIG. 16 is a rear elevational view of the exterior of an alternative embodiment of a pad according to the present invention.
Figure 17:
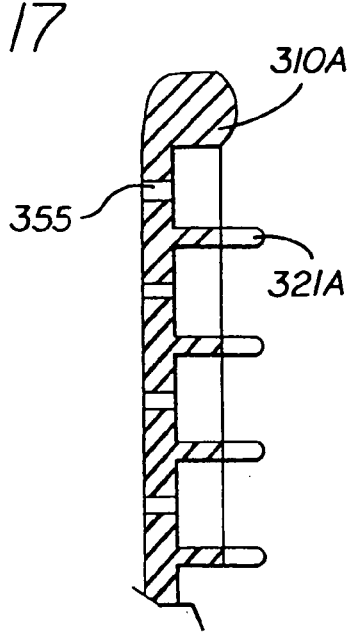
FIG. 17 is a cross-sectional view taken across line 17—17 of FIG. 16.

Another alternative embodiment of the orthopaedic support of the present invention is illustrated by FIG. 15. The heel member 250 comprises a bladder 252 linked via channels 254, 256 to the ankle supports which has its TPE pads 110g configured as bladders as well. Each time the foot of the wearer presses down on the heel member 250, the air or the fluid within the bladder 252 is pressured into the bladder-pad 110g of the ankle supports thereby massaging the lower leg. The pads or bladders 110g may be as shown in earlier figures of the drawing, and may have channels 163a interconnecting the cells of the pads. The channels 254, 256 may be formed integrally with the heel bladder 252, or separate air channels or tubes may be provided to interconnect the heel bladder 252 with the side pads 110g.

Figure 20:
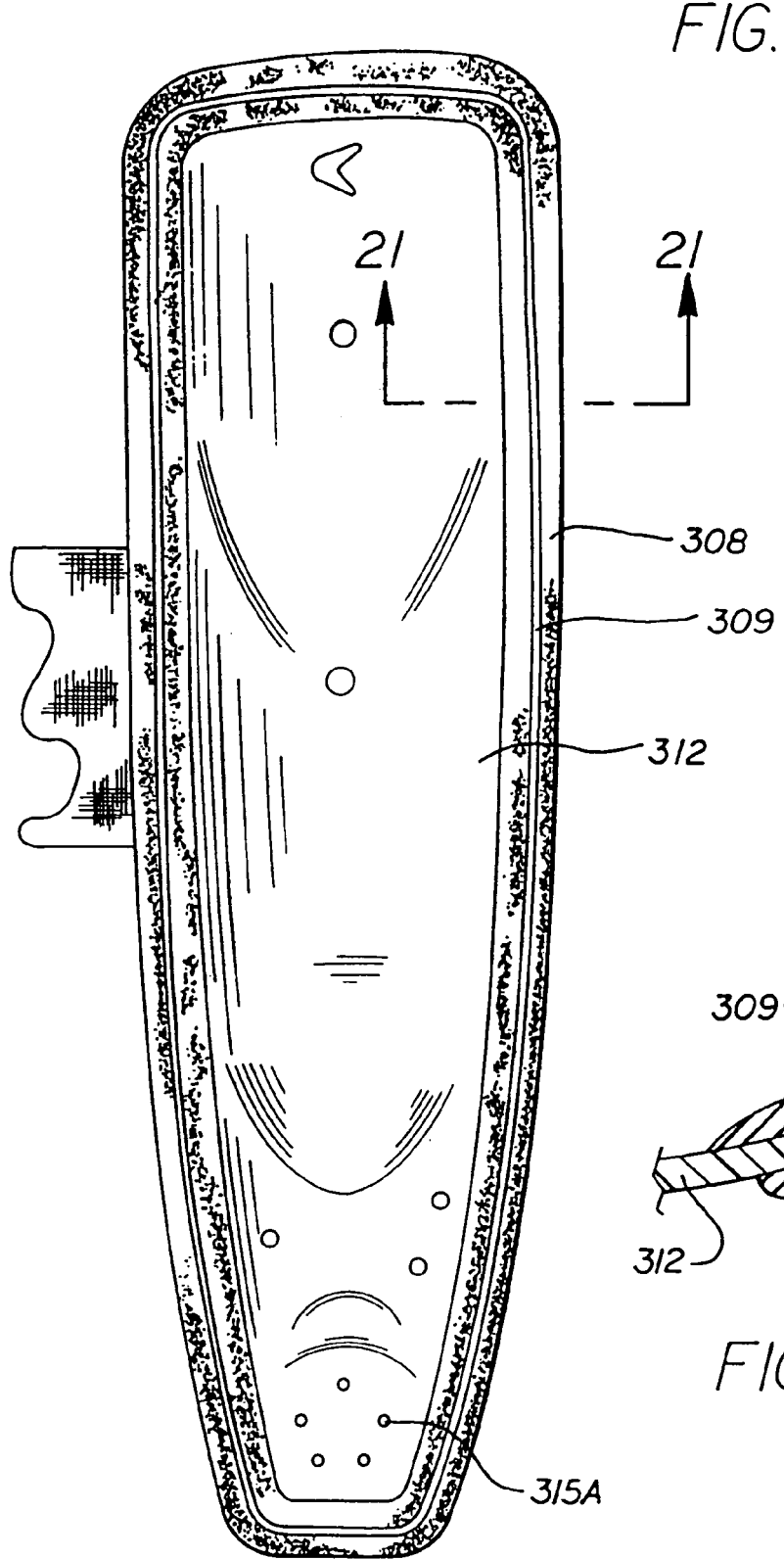
FIG. 20 is a perspective view of a shell to which the pad of FIG. 16 is to be bonded.

FIGS. 16–20 illustrate a further alternative embodiment of the present invention. In this embodiment, the support is provided with a plurality of thin "fingers" 321, which are most clearly seen in FIGS. 17 and 18. The fingers 321 are molded about the periphery of the respective honeycomb cells 352 and 353. The fingers extend from the molded interior elastomer pad 310 of the support to the hard outer plastic shell 312 (FIG. 20). The entire interior elastomer pad 310, which has an edge 310a, can be molded in a single injection molding step to simplify manufacturing.

Figure 18:
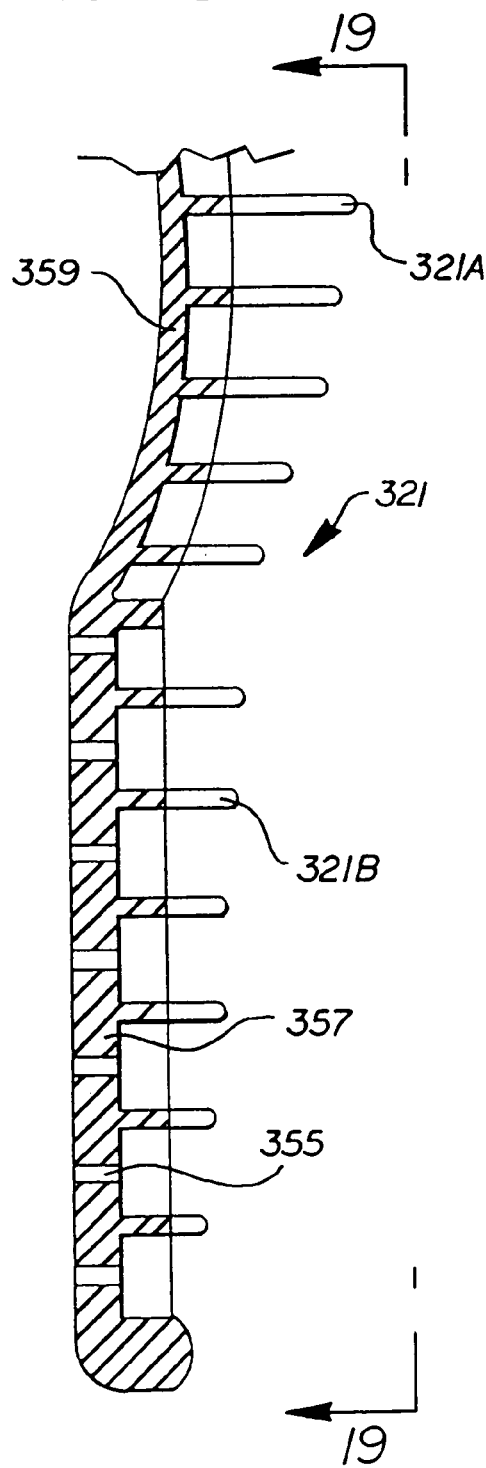
FIG. 18 is a cross-sectional view taken across line 18—18 of FIG. 16.
Figure 19:
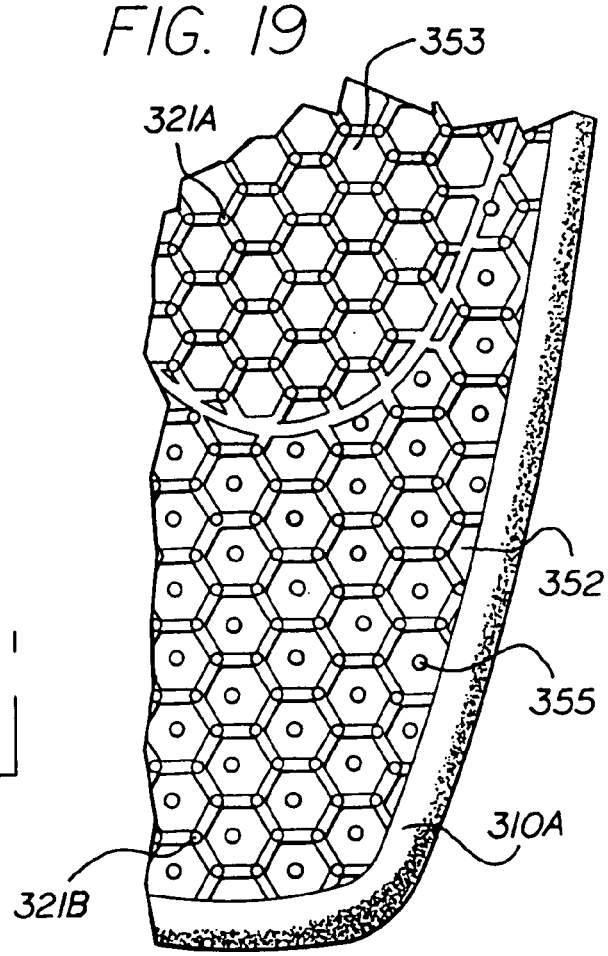
FIG. 19 is a detail perspective view of an interior portion of the pad of FIG. 16.

The aspect ratio of the fingers 321 are varied to provide more or less cushioning in particular regions of the support. For example, FIG. 18 illustrates the change in finger heights in different regions of the pad, including longer fingers 321a and shorter fingers 321b. In much of the support, the fingers 321b are relatively short with respect to the diameter of the fingers. On the other hand, the fingers 321a are considerably longer than the fingers 321b in the rest of the pad. Consequently, the area or areas of the support having the longer fingers 321a will provide more cushioning than the areas of the support having the shorter fingers 321b. That is, the longer fingers 321a flex more than the shorter fingers 321b in response to pressure on the support from the ankle.

The fingers 321a,b also serve to space the flexible inner portion of the support from the hard outer portion of the support. Consequently, the longer fingers 321a provide additional space between the malleous of the ankle and the hard outer shell 312 of the brace. The malleolar region of the ankle is typically where the ankle is injured, and the injury may be exacerbated if the injured portion of the ankle hits the hard outer shell of the support. The longer fingers prevent the malleous from hitting the hard outer shell during use, and provide softer cushioning which makes the brace more comfortable for the wearer during healing.

It should be noted that the outer shell 312 in FIG. 20 includes air holes 315a that allow air within the support to ventilate in and out. In this embodiment of the invention, the cells support the ankle without the need for pressurized air. That is, the structure of the cells themselves rather than pressurized air provide the support for the ankle. This is in contrast to pressurized-air types of supports, which do not provide cushioning unless the support is inflated prior to use.

Additional air holes 355 may be included in the pad 310 itself. For example, the pad 310 in FIG. 16 has numerous air holes in both the bottom and top portions of the pad. Consequently, air is free to flow in and out of the spaces between the pad and the shell. This may be advantageous in, for example, high altitude locations where the air pressure in an air-filled bladder relative to the ambient pressure may become greater than desirable. The present embodiment of the pad, which does not inflate with air, therefore does not have a problem with air pressure in high altitudes.

As an additional alternative, the thickness of the pad walls may vary in different regions of the pad. For example, the wall thickness of the pad of FIG. 18 is greater in the lower region of the pad 357 than in rest of the pad 359. This is because the lower region of the pad generally corresponds to the area of the ankle that is injured and where there is swelling. Increasing the thickness of the skin causes the pad to feel firmer, and decreasing the thickness makes the pad feel softer.

A pad having varying skin thickness is preferably formed by injection molding. However, other methods in which a liquid material solidifies to form to the shape of the mold, such as (for example) reaction-injection molding or pour molding may be employed. To vary the thickness of the skin of the pad while at the same time forming a pad cell structure and integral fingers generally requires a manufacturing method in which a liquid material fills a cavity defining the desired pad configuration, then solidifying to conform the shape of the pad to the shape of the cavity.

Figure 21:
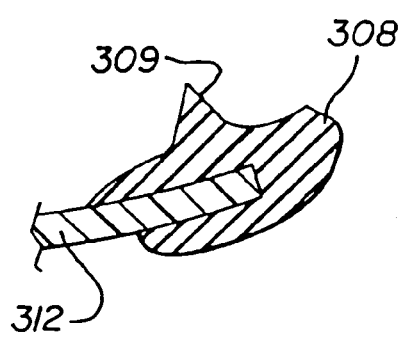
FIG. 21 is a cross-sectional view taken along line 21—21 of FIG. 20 illustrating the overmold that is molded about the edges of the shell itself.

Referring in particular to FIGS. 20 and 21, the shell 312 is provided with an overmold 308 that extends about the periphery of the shell. The overmold is typically formed of the same material as the pad 310, so that the pad can be easily bonded to the overmold. The overmold 308 has a ridge 309 about which the outer edge 310a of the pad extends when the pad is bonded to the overmold. The fingers 321 extend from the pad 310 to the shell 312, with the outer surface of the pad 310 being substantially continuous.

In the presently preferred embodiment, the pad 310 bonds only to the overmold 308 to secure the pad to the shell. The pad is typically bonded to the overmold with a conventional solvent that melts material on both the edge 310a of the pad and on the overmold. The melted material then solidifies to form the bond. However, the pad may be bonded to the overmold in other ways, such as by welding or with adhesives. In alternative embodiments, the pad may be adhered directly to the shell.

In the preferred embodiment of the present invention as illustrated by FIGS. 1–15, a comfortable orthopaedic support is implemented with ankle supports and a heel strap. The ankle supports comprise a rigid shell and padding made from molded thermoplastic elastomer (TPE) with or without other padding material. The TPE pad may be sealed to the shell with trapped air or fluid between the pad and the shell to form a bladder. A lining material may cover the pad. To provide localized comfort, the TPE pad may be molded to include various protrusions or cells toward the shell. These cells may be shaped as domes or other geometric shapes such as honeycomb shapes. Alternatively, soft foam may be embedded between the rigid shell and the durable TPE padding to provide durable surface with soft padding. Another option is to use gel in place of the soft foam or the molded TPE pad. Typically, the overmold which seals the TPE pad to the shell is made of same TPE material as the padding and also partially covers the shell.

Although the present invention has been described in detail with regarding the exemplary embodiments and drawings thereof and with regarding alternate embodiments, it should be apparent to those skilled in the art that various adaptations and modifications of the present invention may be accomplished without departing from the spirit and the scope of the invention. Thus, by way of example and not of limitation, the present invention has been described as an ankle support. However, it is apparent that the inventive support may be applied to arms, legs, and other part of the body requiring varying degrees of localized comfort. Incidentally, where reference is made hereto to air cells or geometric cells, reference is to macro-cells with dimensions greater than 1/64 or 1/32 of an inch for example, and not to foams. Accordingly, the invention is not limited to the precise embodiment shown in the drawings and described in detail hereinabove.

Pads according to some of the embodiments of the present invention may be sealed, such that a space is formed between the pad and the shell that can be filled with air or other fluid to form a fluid bladder. The shell may include an air pump with which the user can inflate the bladder. A release valve can be provided permitting the user to release air from the bladder as necessary.

It should be noted that the cell structure described in connection with the present invention has additional applications. For example, open cells can be inserted in between two layers of material which together form a bladder. The cells act as reinforcement to the bladder, such that if the bladder deflates or if an especially great load is applied to the bladder, the cell structure reduce the likelihood that the bladder will bottom out.

While a pad made with a TPE material has been described, and while the inventors presently prefer to make the pad from TPE material, it should be understood that the pad may be made from a variety of other materials. For example (but without limitation) the pad may be made of thermoplastic urethanes, thermoplastic rubbers, silicones, two-part urethane mixtures and poured foams.

It should be noted that the fingers 321 are shown in the figures as having a generally circular cross-section. However, the fingers can have various other cross-sections, so long as they perform a cushioning function.

While the pads described herein are particularly well suited for use in orthopaedic supports, there are numerous other applications in which such pads could be employed. For example, embodiments of this type of pad may be employed in various protective devices, such as knee pads, shin guards, and football pads, among other applications where durability and water resistance are desired.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited solely by the claims appended hereto. It is therefore intended that the following claims may be interpreted as covering all such applications, alterations and modifications as fall within the true spirit and scope of the invention.

We claim:

1. An orthopaedic support for comfortably supporting the ankle of a wearer, comprising:
    an outer shell formed for fitting about the lower leg of the wearer;
    a molded pad bonded to said shell;
    an overmold that substantially surrounds said pad and said shell substantially sealing together said orthopaedic support;
    said pad having a base layer;
    said pad having a plurality of molded substantially hollow structures to provide differing levels of cushioning support for the wearer of the orthopaedic support at different areas of the pad, at least some of said structures having a different dimension than others of said structures; and
    said hollow structures extending substantially perpendicular from said base layer;
    said hollow structures being integrally molded with said base layer;
    wherein said molded structures comprise walls, said walls providing cushioning support for the ankle and having a self supporting free standing construction even without inflating or otherwise filling said molded structures with air, liquid, or gel.

2. An orthopaedic support as defined in claim 1 further comprising an overmold molded onto said shell, said pad being bonded to said overmold.

3. An orthopaedic support as defined in claim 1 further comprising means for securing said ankle support around the lower leg; and a heel strap for securing said orthopaedic support.

4. An orthopaedic support as defined in claim 1 wherein an inner liner of cloth is secured to said pad on the surface of said pad facing the lower leg of the user.

5. An orthopaedic support as defined in claim 4 wherein said liner is integrated with said pad.

6. An orthopaedic support in accordance with claim 5 wherein said liner includes openings allowing air to pass in and out of said structures.

7. An orthopaedic support as defined in claim 1, wherein said pad further comprised a plurality of fingers extending from said pad to said outer shell.

8. An orthopaedic support as defined in claim 7, wherein said fingers are integrally molded with said pad.

9. An orthopaedic support as defined in claim 7, wherein some of said fingers have a different length than others of said fingers.

10. An orthopaedic support for comfortably supporting a select area of the anatomy, said support comprising:
   a substantially rigid shell; and
   an injection molded resilient pad between said shell and the anatomy of the user, said pad configured with geometric shaped cells providing cushioning and support wherein said pad is molded directly onto said shell as channels, domes, and other supportive geometrical shapes to cushion and to support the anatomy;
   said pad including a base layer, and said cells being integrally molded with said base layer and extending substantially perpendicular from said base layer;
   wherein said cells comprise walls, the structure of said walls providing cushioning support for the select area of the anatomy and having a self-supporting freestanding construction even without inflating the cells with air or otherwise filling said cells with liquid, or gel.

11. An orthopaedic support as defined in claim 10 further comprising an overmold molded onto said shell, said pad being connected to said overmold.

12. An orthopaedic support as defined in claim 10 wherein said pad is a bladder having a plurality of cells having cushioning geometric shapes and protrusions, each cell with predetermined size, depth, and wall thickness providing varying levels of localized support and cushion in different areas of said support.

13. An orthopaedic support as defined in claim 12 wherein said geometric shapes for said bladder are selected from the group consisting of ribs, cylinders, honeycomb, and regular and irregular polygons.

14. An orthopaedic support as defined in claim 12 wherein channels are provided between said cells for allowing a fluid to pass between and among said cells, creating a massaging effect on the ankle and promoting blood flow.

15. An orthopaedic support as defined in claim 10 wherein said pad further comprises a foam core for softer inner cushion.

16. An orthopaedic support as defined in claim 10 wherein a co-molded lip around said shell and around said pad seals said pad such that air is trapped between said pad and said shell, creating a bladder with air cushion.

17. An orthopaedic support as defined in claim 10 wherein said pad includes a plurality of fingers extending from said pad to said shell.

18. An orthopaedic support comprising:
   a substantially rigid shell formed to fit a limb of a user;
   an injection molded resilient pad for cushioning the shell to the limb wherein said pad includes interconnected cells, and further comprises a heel bladder fluidically coupled to said pad for varying the pressure exerted by said pad on the limb of the user;
   said injection molded pad being integrally molded in a single molding step; and
   said pad including a base layer and integrally molded structures protruding from said base layer, said structures having a self supporting free standing construction even without inflating or otherwise filling said structures with air, liquid, or gel.

19. An orthopaedic support pad as defined in claim 18 wherein said pad is a bladder having geometrically shaped cells to provide differing levels of localized cushioning and a plurality of channels molded between said cells to allow air and fluid to pass between said cells.

20. An orthopaedic support as defined in claim 18 wherein a breathable liner covers said pad.

21. An orthopaedic support as defined in claim 18 wherein said pad includes a plurality of integrally-molded fingers extending from said pad to said shell.

22. An orthopaedic support as defined in claim 18 further comprising an overmold molded onto said shell.

23. An orthopaedic support for comfortably supporting the ankle comprising:
   an ankle support formed for fitting about the lower leg; having appropriate configuration to support the ankle;
   said ankle support comprising a substantially rigid outer shell and a molded pad for cushioning;
   said pad having a base layer and an inner construction including resilient material having cells therein for providing resilient support to the ankle;
   said base layer and said cells being integrally molded together;
   said pad being bonded to said outer shell; and
   wherein said outer shell has a least one opening to allow air to escape from space in between said outer shell and said pad, said cells providing resilient support to the ankle from the structure of the cells and having a self supporting free standing construction even without being filled with air, liquid, or gel.

24. An orthopaedic support as defined in claim 23 wherein at least some of said air spaces are filled with foam for cushioning.

25. An orthopaedic support as defined in claim 23 wherein said pad includes a plurality of fingers extending from said pad toward said shell.

26. An orthopaedic support as defined in claim 23 further comprising an overmold molded onto said shell.

27. An orthopaedic support as defined in claim 26 wherein said pad is bonded to said overmold.

28. An orthopaedic support as defined in claim 23 wherein said pad includes a plurality of air holes to prevent formation of a bladder between said pad and said shell.

29. An orthopaedic support for comfortably supporting the ankle of a wearer, comprising:
   an outer shell formed for fitting about the lower leg of the wearer;
   a molded pad bonded to said shell;
   said pad having a surface; and
   said pad having a plurality of molded structures to provide differing levels of cushioning support for the wearer of the orthopaedic support at different areas of the pad, at least some of said structures having a different dimension than others of said structures;
   wherein said pad further comprises a plurality of fingers extending from said pad to said outer shell;
   some of said fingers having a different length than others of said fingers; and
   said support having a malleolar region that is adapted to be placed against a malleolus of an ankle, said malleolar region having fingers of a greater length than fingers in other regions of said support.

30. An orthopaedic support comprising:
   a substantially rigid shell formed to fit a limb of a user;
   an injection molded pad for cushioning the shell to the limb;
   said injection molded pad being integrally molded in a single molding step;
   wherein said pad is a bladder having geometrically shaped cells to provide differing levels of localized cushioning and a plurality of channels molded between said cells to allow air and fluid to pass between said cells;
   wherein at least one cell defines a closed space forming an internal bladder.

31. An orthopaedic support for comfortably supporting the ankle comprising:
- an ankle support formed for fitting about the lower leg, adapted to support the ankle;
- said ankle support comprising a substantially rigid outer shell and a molded pad for cushioning;
- said pad having an inner surface and an outer layer, said inner surface including resilient material having cells therein for providing resilient support to the ankle; and
- said pad being bonded to said outer shell;
- wherein said outer shell has at least one opening to allow air to escape from space in between said outer shell and said pad, said cells providing resilient support to the ankle from the structure of the cells even without being filled with air;
- wherein said orthopaedic support further comprises an overmold molded onto said shell;
- wherein said pad is bonded to said overmold; and
- wherein said overmold includes a ridge extending about the periphery of the overmold, said pad having an outer edge that engages with said ridge.

32. An orthopaedic support for comfortably supporting the ankle comprising:
- an ankle support formed for fitting about the lower leg, adapted to support the ankle;
- said ankle support comprising a substantially rigid outer shell and a molded pad for cushioning;
- said pad having an inner surface and an outer layer, said inner surface including resilient material having cells therein for providing resilient support to the ankle; and
- said pad being bonded to said outer shell;
- wherein said outer shell has at least one opening to allow air to escape from space in between said outer shell and said pad, said cells providing resilient support to the ankle from the structure of the cells even without being filled with air; and
- wherein said pad has a non-uniform skin thickness, said pad having at least one region having skin that is thicker than at least one other region, in order to improve the function of the support.

33. An orthopaedic support for comfortably supporting the ankle of a wearer, comprising:
- an outer shell formed for fitting about the lower leg of the wearer;
- a molded pad bonded to said shell;
- said pad having a surface;
- said pad having a plurality of molded substantially hollow structures to provide differing levels of cushioning support for the wearer of the orthopaedic support at different areas of the pad, at least some of said structures having a different dimension than others of said structures;
- wherein said molded structures comprise walls, said walls providing cushioning support for the ankle even without inflating or otherwise filling said molded structures with air, liquid, or gel; and
- said pad further comprising a plurality of fingers extending from said pad to said outer shell, said fingers being integrally molded with said pad; and some of said fingers having a different length than others of said fingers.

34. An orthopaedic support comprising:
- a substantially rigid shell formed to fit a limb of a user;
- an injection molded pad for cushioning the shell to the limb;
- said injection molded pad being integrally molded in a single molding step; and
- wherein said shell further comprises a shell frame and a shell core which is removably mounted within said shell.

35. An orthopaedic support for comfortably supporting the ankle comprising:
- an ankle support formed for fitting bout the lower leg, having appropriate configuration to support the ankle;
- said ankle support comprising a substantially rigid outer shell and a molded pad for cushioning;
- said pad having an inner surface and an outer layer; said inner surface including resilient material having cells therein for providing resilient support to the ankle;
- said pad being bonded to said outer shell;
- wherein said outer shell has at least one opening to allow air to escape from space in between said outer shell and said pad, said cells providing resilient support to the ankle from the structure of the cells even without being filled with air, liquid, or gel;
- wherein at least some of said air spaces are filled with foam for cushioning, and said foam surrounds but does not cover the malleolus.

36. An orthopaedic support for comfortably supporting the ankle comprising:
- an ankle support formed for fitting about the lower leg, having appropriate configuration to support the ankle;
- said ankle support comprising a substantially rigid outer shell and a molded pad for cushioning;
- said pad having an inner surface and an outer layer; said inner surface including resilient material having cells therein for providing resilient support to the ankle; and
- said pad being bonded to said outer shell;
- wherein said outer shell has at least one opening to allow air to escape from space in between said outer shell and said pad, said cells providing resilient support to the ankle from the structure of the cells even without being filled with air, liquid, or gel; and
- an overmold molded onto said shell, with said pad being bonded to said overmold, and said overmold including a ridge extending about the periphery of the overmold, said pad having an outer edge that engages with said ridge.

37. An orthopaedic support for comfortably supporting the ankle comprising:
- an ankle support formed for fitting about the lower leg, having appropriate configuration to support the ankle;
- said ankle support comprising a substantially rigid outer shell and a molded pad for cushioning;
- said pad having an inner surface and an outer layer; said inner surface including resilient material having cells therein for providing resilient support to the ankle; and
- said pad being bonded to said outer shell;
- wherein said outer shell has at least one opening to allow air to escape from space in between said outer shell and said pad, said cells providing resilient support to the ankle from the structure of the cells even without being filled with air, liquid, or gel; and
- said pad having a non-uniform skin thickness, said pad having at lest one region having skin that is thicker than at least one other region, in order to improve the function of the support.

* * * * *

UNITED STATES PATENT AND TRADEMARK OFFICE
CERTIFICATE OF CORRECTION

| | | |
|---|---|---|
| PATENT NO. | : 7,018,351 B1 | Page 1 of 1 |
| APPLICATION NO. | : 09/857396 | |
| DATED | : March 28, 2006 | |
| INVENTOR(S) | : Joseph M. Iglesias et al. | |

It is certified that error appears in the above-identified patent and that said Letters Patent is hereby corrected as shown below:

Column 1,
Cancel lines 7 - 10 and insert new paragraph -- The present application is a national phase entry of international application no. PCT/US97/15265 filed August 29, 1997 under the Patent Cooperative Treaty, which is a continuation-in-part of U.S. serial no. 08/705,218, filed August 29, 1996, now abandoned, all of whose contents are hereby incorporated by reference. --

Signed and Sealed this

Third Day of October, 2006

JON W. DUDAS
*Director of the United States Patent and Trademark Office*